(12) United States Patent
Chang et al.

(10) Patent No.: US 12,083,000 B2
(45) Date of Patent: Sep. 10, 2024

(54) PHYSIOLOGICAL PANTS

(71) Applicants: Hui-Ting Chang, Pingtung County (TW); Ya-Wen Ko, Taipei (TW)

(72) Inventors: Hui-Ting Chang, Pingtung County (TW); Ya-Wen Ko, Taipei (TW)

( * ) Notice: Subject to any disclaimer, the term of this patent is extended or adjusted under 35 U.S.C. 154(b) by 952 days.

(21) Appl. No.: 17/097,512

(22) Filed: Nov. 13, 2020

(65) Prior Publication Data

US 2021/0212864 A1 Jul. 15, 2021

(30) Foreign Application Priority Data

Jan. 14, 2020 (TW) ................................. 109101260

(51) Int. Cl.
*A61F 13/15* (2006.01)
*A61F 13/514* (2006.01)
*A61F 13/515* (2006.01)
*A61F 13/66* (2006.01)
*A61F 13/72* (2006.01)

(52) U.S. Cl.
CPC .. *A61F 13/15268* (2013.01); *A61F 13/51456* (2013.01); *A61F 13/515* (2013.01); *A61F 13/665* (2013.01); *A61F 13/72* (2013.01); *A61F 2013/15276* (2013.01)

(58) Field of Classification Search
CPC .... A61F 13/47; A61F 13/62; A61F 13/15268; A61F 13/51456; A61F 13/515; A61F 13/665; A61F 13/72; A61F 2013/15276; A61F 13/5123; A61F 13/494; A61F 2013/49493; A61F 13/565; A61F 13/514; A41B 9/00; A41B 9/001; A41B 9/002; A41B 9/003; A41B 9/004; A41B 9/005; A41B 9/006; A41B 9/007; A41B 9/008; A41B 9/009; A41B 9/001; A41B 9/0011; A41B 9/0012; A41B 9/0013; A41B 9/0014; A41B 9/0015; A41B 9/0016; A41B 9/04

See application file for complete search history.

(56) References Cited

U.S. PATENT DOCUMENTS 3,929,135 A * 12/1975 Thompson ................ B32B 3/28
604/374
4,213,813 A * 7/1980 Hendricks ............. A61F 13/515
156/227

(Continued)

*Primary Examiner* — Benjamin J Klein
*Assistant Examiner* — Rachel O'Connell
(74) *Attorney, Agent, or Firm* — Rabin & Berdo, P.C.

(57) ABSTRACT

The physiological pants of the present invention comprise: a clothing layer, a waterproof layer, a water storage layer and a water-permeable layer; the clothing layer constructs a clothing; the waterproof layer is a surrounding wall to enclose the water storage space; the water-permeable layer and the water storage layer are arranged in the water storage space; wherein, the water-permeable layer includes a first layer body and a second layer body. The first layer body is formed with a plurality of first water-permeable holes, and the second layer body is formed with a plurality of second water-permeable holes smaller than the first water-permeable hole, so that a plurality of tapered holes are collectively formed inside the water-permeable layer by the first water-permeable hole and the second water-permeable hole, so as to prevent the liquid in the water storage layer from easily passing through the water-permeable layer when the water storage layer is squeezed.

10 Claims, 7 Drawing Sheets

(56) References Cited

U.S. PATENT DOCUMENTS

| | | | | |
|---|---|---|---|---|
| 5,643,239 | A * | 7/1997 | Bodford | A61F 13/51405 |
| | | | | 604/366 |
| 8,476,483 | B2 * | 7/2013 | Yoshimasa | A61F 13/8405 |
| | | | | 604/360 |
| 2008/0065039 | A1 * | 3/2008 | Labit | A61F 13/5633 |
| | | | | 604/385.15 |
| 2016/0129626 | A1 * | 5/2016 | Arora | B32B 3/06 |
| 2020/0214637 | A1 * | 7/2020 | Brownhill | A61B 5/0071 |

* cited by examiner

PHYSIOLOGICAL PANTS

FIELD OF THE INVENTION

The present invention relates to a kind of clothing, and more particularly, to a kind of physiological pants used by women.

BACKGROUND

Sanitary pad is a product that solves the inconvenience caused by women's physiology. At present, most mainstream sanitary pads are disposable products. Although based on hygienic considerations, this disposable product can solve the hygiene problem, and because it is thrown away once used, in the choice of internal absorbent materials, materials of strong water absorption but one-off might be used.

However, the resources consumed in the production of such disposable products are also very considerable over time and greatly increases the volume of waste.

SUMMARY

The main purpose of the present invention is to provide a physiological pants with a water-absorbing layer that can be reused after air drying. The water-absorbing layer is provided with a water-permeable layer that allows liquid to more easily pass in a single direction, and can be reused.

To achieve the above purpose, the physiological pants of the present invention comprises: a clothing layer, a waterproof layer, a water storage layer and a water-permeable layer.

The clothing layer constructs clothing, and the clothing is formed with a main opening for the torso to pass through and two secondary openings for the limbs to pass through; the waterproof layer is attached to the clothing layer, and the waterproof layer is formed as a surrounding wall to enclose a water storage space with a water absorbing opening; the water storage layer is arranged at the bottom of the water storage space; and the water-permeable layer is arranged in the water storage space and contacts with a surface of the water storage layer close to the water absorbing opening, wherein the water-permeable layer contains an antibacterial agent.

Wherein, the water-permeable layer includes a first layer body woven by a plurality of first threads and a second layer body woven by a plurality of second threads. The first layer body is formed with a plurality of first water-permeable holes, and the second layer body is formed with a plurality of second water-permeable holes smaller than the first water-permeable holes. As a result, a plurality of tapered holes are jointly formed inside the water-permeable by the first water-permeable holes and the second water-permeable holes.

Regarding how to form the tapered hole, in one embodiment, the thread diameter of the first thread is smaller than the thread diameter of the second thread, and the distance on centerline between the first threads in the first layer body is equal to the distance on centerline between the second threads in the second layer body.

In another embodiment, the thread diameter of the first thread is smaller than the thread diameter of the second thread, and the distance on centerline between the first threads in the first layer body is larger than the distance on centerline between the second threads in the second layer body.

In yet another embodiment, the thread diameter of the first thread is larger than the thread diameter of the second thread, and the distance on centerline between the first threads in the first layer body is larger than the distance on centerline between the second threads in the second layer body.

In a preferred embodiment, the waterproof layer, the water storage layer, and the water permeable layer together form a sanitary pad. Two opposite sides of the sanitary pad are respectively formed as a curved portion corresponding to the shape of the secondary openings, and the remaining sides of the sanitary pad are respectively formed as two edges of different length, a first edge with and a second edge larger than the first edge.

And in the present embodiment, the clothing layer is formed with an inner folder for covering the curved portion adjacent to the secondary opening, and the clothing layer has a first attachment area for attaching the first edge of the sanitary pad and a second attachment area for attaching the second edge of the sanitary pad; wherein, the sanitary pad is fixed to the clothing layer through a plurality of seals, the sanitary pad is covered by a part of the seal. When connected, one of the first attachment area and the second attachment area is covered by the other part of the seal.

In the preferred embodiment, the waterproof layer, the water storage layer and the water-permeable layer are connected to each other by stitching. The water storage layer is a water-absorbing pad that can be reused after air drying; the periphery of the water storage layer is formed as a connecting portion for connecting the water-permeable layer directly, so that a gap is formed between the water storage layer and the water-permeable layer for holding the liquid.

As can be seen from the above description, the present invention features a water storage layer that can be reused after air drying, and in order to prevent the liquid stored in the water storage layer from easily leaving the water storage layer when being squeezed, the water-permeable layer on the surface of the water storage layer is provided with tapered holes that allow liquid to easily pass through the water-permeable layer in single direction; wherein, in the way of forming the tapered holes, the water-permeable layer has two layer bodies formed with water-permeable holes, and the sizes of the water-permeable holes on each layer body are different. Through contact between the two layer bodies, holes of different sizes in the layer bodies are connected to each other to form the tapered holes of the water-permeable layer.

DETAILED DESCRIPTION OF PREFERRED EMBODIMENTS

Figure 1:
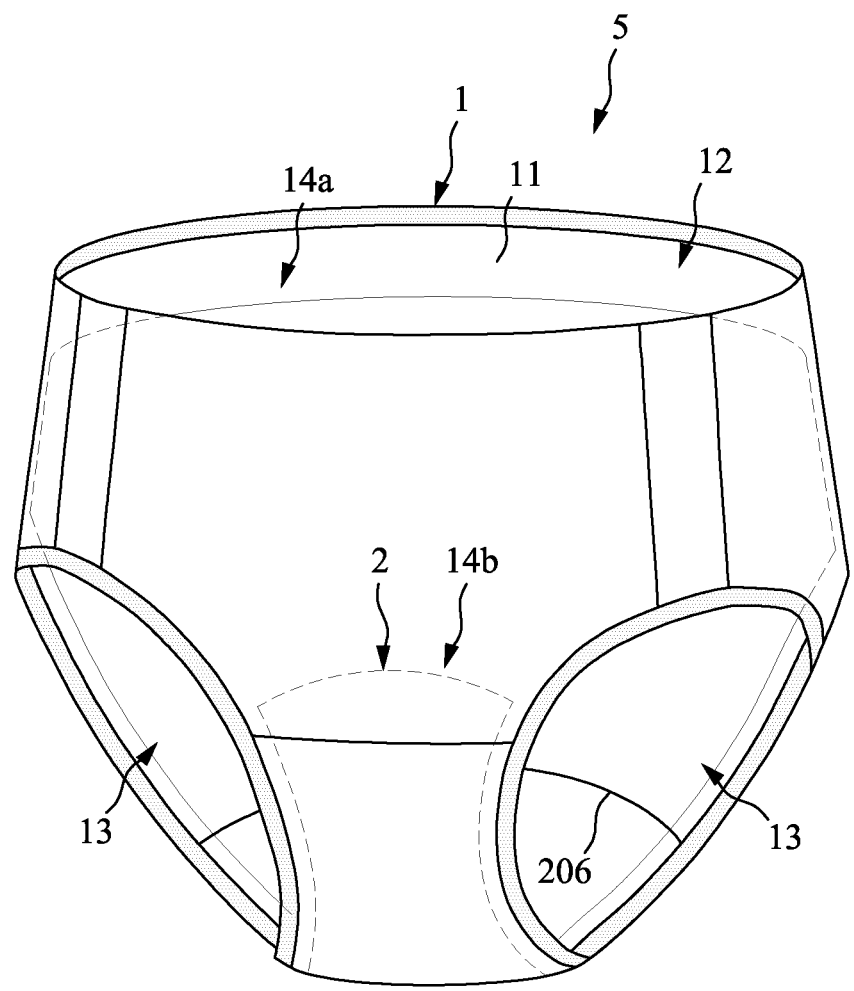
FIG. 1 is a schematic illustrating the physiological pants of the present invention according to an embodiment.

In order to further understand the structure, usage and features of the present invention more clearly and in detail, the present invention is described in detail below with references to the accompanying drawings and specific preferred embodiments:

Please refer to FIGS. 1 to 3B. In a preferred embodiment, the physiological pants 5 of the present invention includes: a piece of clothing 1 and a sanitary pad 2. The clothing 1 is made by cutting and sewing a clothing layer 10 (see FIGS. 3A and 3B), and a through space 11 is formed inside the clothing 1. Before using, the through space 11 is initially formed with a main opening 12 and two secondary openings 13, the main opening 12 is for user's torso to pass through and communicates with the inner and outer sides of the through space 11, and the secondary openings 13 are for the user's limbs (feet) to pass through; in order to install in position aligned with the sanitary pad 2, one position of the clothing 1 corresponding to the buttocks is provided with a first adhesive portion 14a, and a second adhesive portion 14b is provided at one position close to the groin; the clothing layer 10 can be made of conventional clothing materials without special restrictions.

Figure 2:
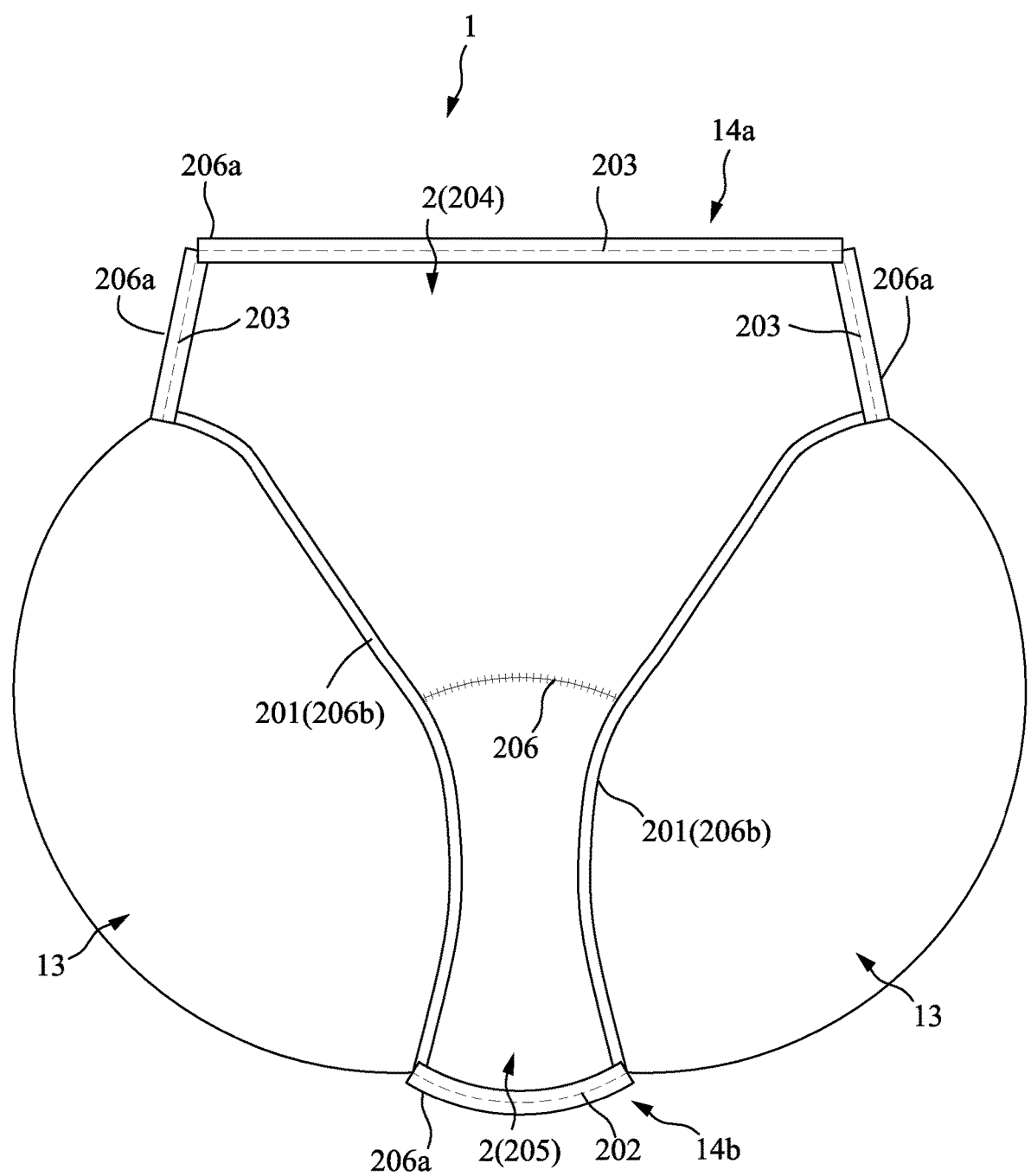
FIG. 2 is a schematic illustrating the installation of the sanitary pad in FIG. 1.

Please refer to FIG. 2, as for the shape of the sanitary pad 2, two opposite sides of the sanitary pad 2 are respectively formed as a curved portion 201 corresponding to the shape of the secondary opening 13, and the remaining sides of the sanitary pad are respectively formed as two edges of different lengths, a first edge 202 and a second edge 203 larger than the first edge 202, furthermore, the sanitary pad 2 is divided into a first area 204 installed at a position of the clothing 1 close to the rear buttocks and a second area 205 located between the two curved portions 201, and the second area 205 is formed with a crease 206.

Figure 3A:
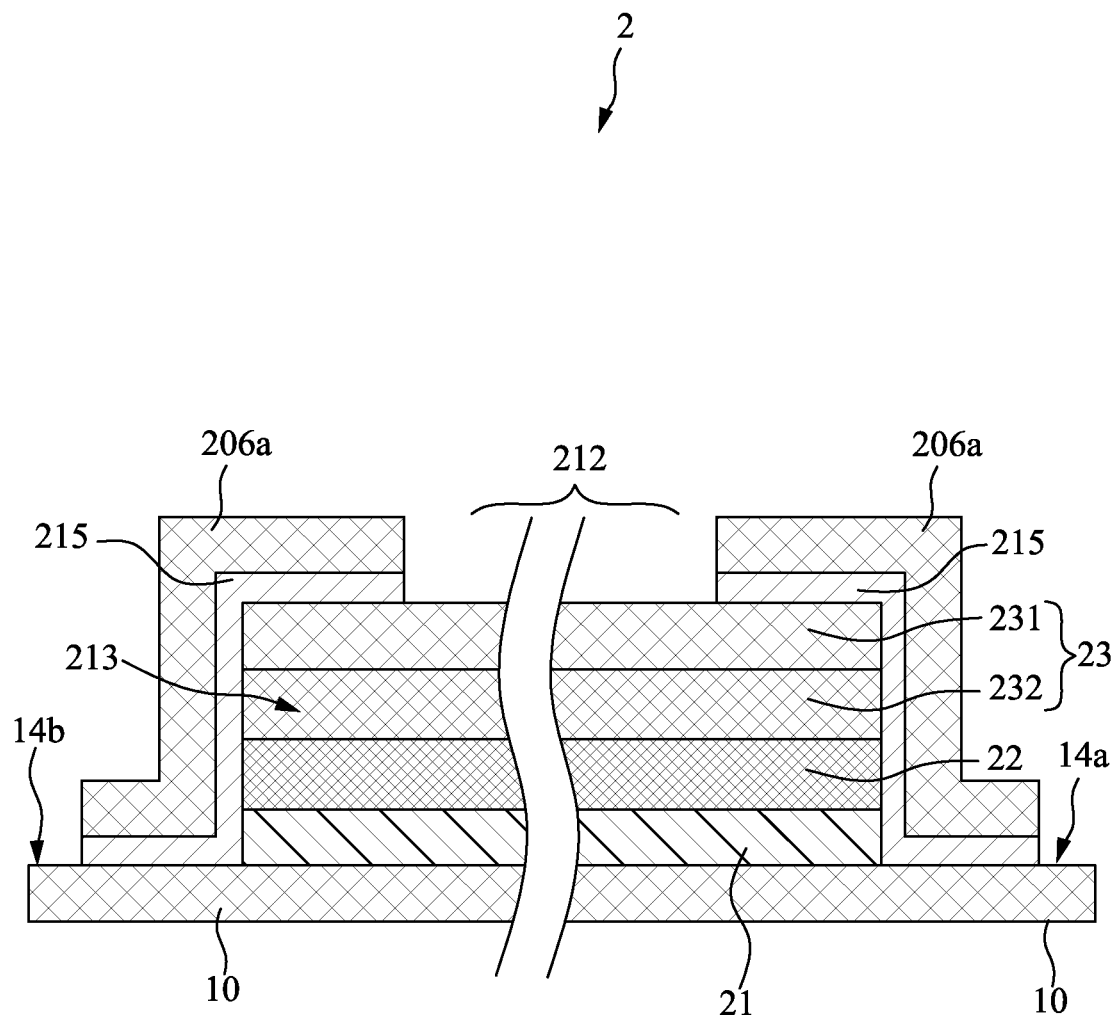
FIG. 3A is a schematic illustrating cross-sectional view of the installation of the sanitary pad on the first side and the second side in FIG. 1.

As shown in FIGS. 2 and 3A, when the clothing 1 is attached to the sanitary pad 2, the edge of the first area 204 of the sanitary pad 2 corresponds to the first adhesive portion 14a, and the edge of the second area 205 also corresponds to the second adhesive portion. The sanitary pad 2 is attached to the clothing 1 through a plurality of seals 206a. When connected, a part of the seal 206a covers and adheres to the edge of the sanitary pad 2 (the assembly of 21, 22, 23), and the other part covers and adheres to the first adhesive part 14a and the second adhesive part 14b; in this embodiment, the seal 206a is made of materials same as the clothing layer 10, and is attached to the sanitary pad 2 through the adhesive layer 215 on its surface. Wherein, there is no limitation on the type of the adhesive layer 215; in some embodiments, it may be ordinary adhesive, and in some embodiments, it may be hot melt adhesive (bonding by thermocompression).

Figure 3B:
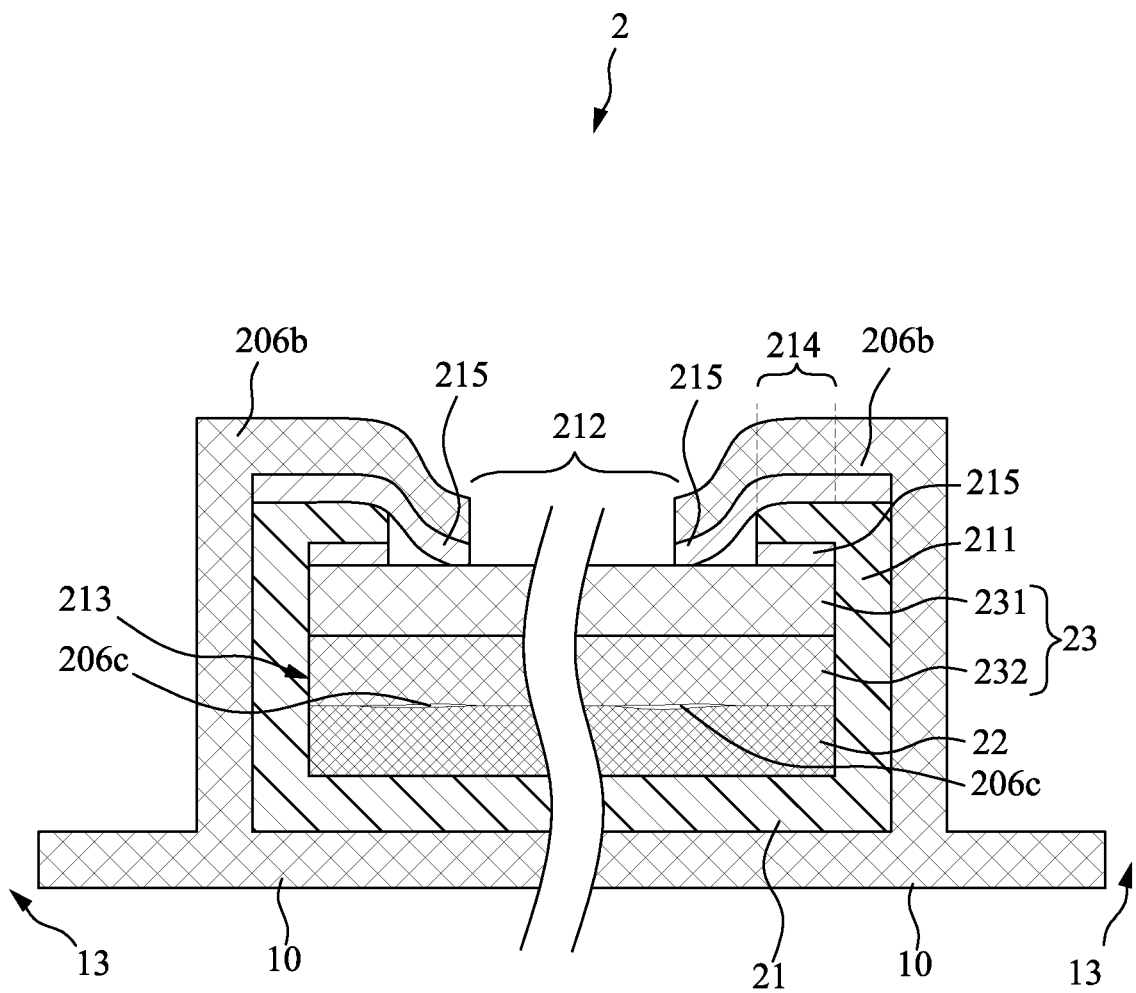
FIG. 3B is a schematic illustrating cross-sectional view of the installation of the sanitary pad in the position of the secondary opening in FIG. 1.

Please refer to FIGS. 2 and 3B, the edge of the secondary opening 13 of the clothing layer 10 is formed with an inner edge 206b, the inner edge 206b extends toward between the two secondary openings 13. When installation, a part of the inner edge 206b covers the sanitary pad 2 and is attached to the sanitary pad 2 through the adhesive layer 215, and one end of the inner edge 206b also forms a bend portion 206c bending toward the sanitary pad 2.

As for structure of the sanitary pad 2, please refer to FIGS. 3A and 3B. The sanitary pad 2 includes: a waterproof layer 21, a water storage layer 22, and a water-permeable layer 23; the water barrier 21, the water storage layer 22, and the water-permeable layer 23 are connected to each other mainly through stitching; the waterproof layer 21 may form at least a part of the surrounding wall 211 as an impermeable layer (see following description), the surrounding wall 211 encloses a water storage space 213 with a water absorbing opening 212, so as to keep the water absorbed by the sanitary pad 2 in the water storage space 213 (in FIG. 3, the thickness among the layers is not drawn according to actual ratio).

The water storage layer 22 is arranged at the bottom of the water storage space 213 and is a water-absorbing pad that can be reused through air drying. In the present embodiment, the water-absorbing pad is made of polyester mixed with rayon. In other embodiments, conventional materials such as non-woven cloth may be used instead.

The water-permeable layer 23 is arranged in the water storage space 213 and contacts with a surface of the water storage layer 22 close to the water absorption opening 212. After treatment, the water-permeable layer 23 contains a releasable antibacterial agent. The type of the antibacterial agent is not limited, the antibacterial agent can use conventional compounds, such as cyclodextrin or metal ions, etc. The water-permeable layer 23 includes a first layer body 231 woven from a first thread 231a and a second layer body 232 woven from a second thread 232a different from the first thread 231a (in this embodiment, for the example, polyester fiber (polyester)). The first layer body 231 is located on one side of the water-permeable layer 23 close to the water absorbing opening 212, and is formed with a plurality of first water-permeable holes 231b; the second layer body 232 is formed with a plurality of second water-permeable holes 232b smaller than the first water-permeable holes 231b. Because the first layer body 231 and the second layer body 232 are adjacent to each other, the water-permeable holes 231b, 232b are connected to each other to form a plurality of tapered holes 233 that facilitates liquid absorption.

In this way, when the liquid contacts the water-permeable layer 23, the liquid will be quickly guided by the first water-permeable holes 231b to the inner second layer body 232; when it comes into contact with the second water-permeable holes 232b, the liquid will quickly diffuse and be absorbed by the water storage layer 22.

Wherein, as for the details of the attachment between the two layers of the sanitary pad and how to form the water storage space, please refer to FIGS. 3A and 3B respectively; in the present embodiment, when the sanitary pad 2 is attached to the first adhesive portion 14a and the second adhesive portion 14b through the seal 206a (as shown in FIG. 3A), the adhesive layer 215 on the seal 206a is not permeable to water, so the adhesive layer 215 on the seal 206a and the waterproof layer 21 jointly enclose the water storage space 213.

When the sanitary pad 2 is attached to the inner edge 206b, as shown in FIG. 3B, between the two secondary openings 13, through the bending of both sides of the waterproof layer 21, the waterproof layer 21 separately forms the surrounding wall 211 as a single element to construct water storage space 213. Wherein, in order to ensure the attachment strength between the waterproof layer 21 and the water permeable layer 23, near the water absorbing opening 212 a position of the surrounding wall 211 is formed with a turned-inward portion 214 extending toward the water absorbing opening 212. The turned-inward portion 214 is connected to the surface of the water-permeable layer 23 through the adhesive layer 215. The inner edge 206b is also connected to the waterproof layer 21 through the adhesive layer 215, and partially covers the water-permeable layer 23 (but there is no particular limit on whether it is connected to the surface of the water-permeable layer 23).

In addition, as shown in FIG. 3B, in the embodiment where the water permeable layer 23, the water storage layer 22, and the waterproof layer 21 are connected by stitching, the stitch tension or the size of the sewing area can be adjusted to make a part of the surface among the layer body (21, 22, 23) formed a connecting portions directly connected to each other and formed gap 206c capable of slightly or partially being separated from each other to further store moisture. The gap 206c is the gap between the water storage layer 22 and the waterproof layer 21 (located at the bottom of the water storage space 213); wherein, in one preferred embodiment, the gap 206c is preferably formed between the water storage layer 22 and the water-permeable layer 23.

Wherein, the present invention has no limit on how to form the tapered hole 233. In addition to the difference in the material itself based on existing knowledge, the thickness and arrangement of the thread itself can also be used to form the tapered hole 233 when using the same material, which can be referred to FIGS. 4A to 4C.

Figure 4A:
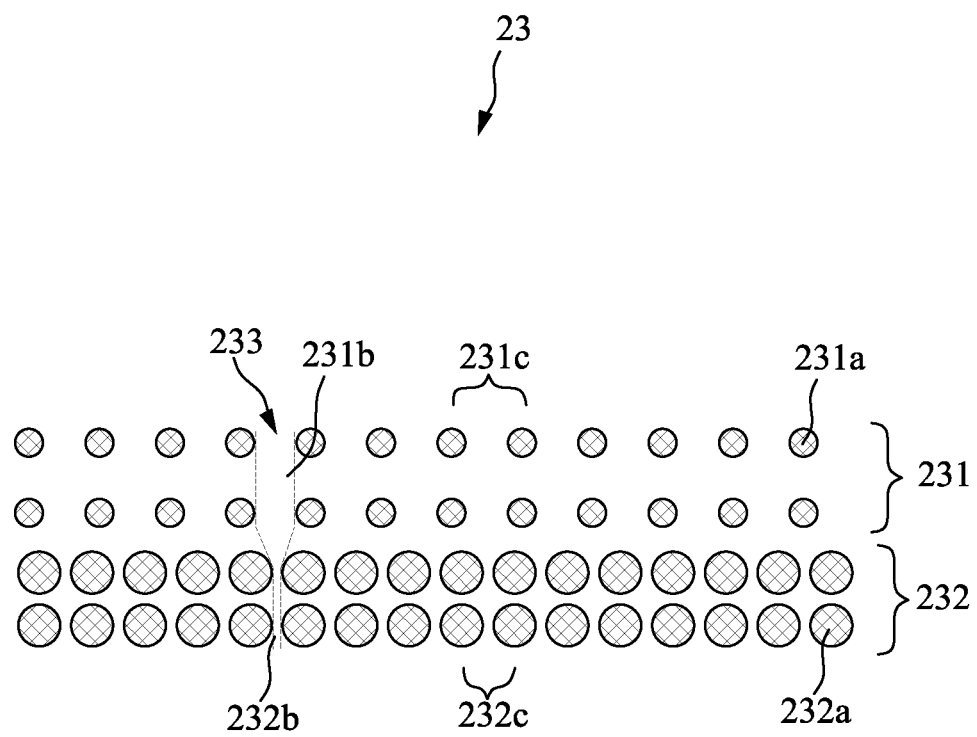
FIG. 4A is a schematic illustrating structure of the water-permeable layer in FIG. 1.

As shown in FIG. 4A, in one type of embodiment, the diameter of the first thread 231a is smaller than that of the second thread 232a, and a distance 231c on center line between first threads 231a in the first layer 231 is greater than a distance 232c on center line between second threads 231a in the second layer body 232, so that the diameter of the first water-permeable hole 231b in the first layer body 231 is larger than the second water-permeable hole 232b, and thus at the contact surface, the first water-permeable hole 231b and the second water-permeable hole 232b jointly form a depression similar to the tapered hole 233 (the dotted line in the figure).

Figure 4B:
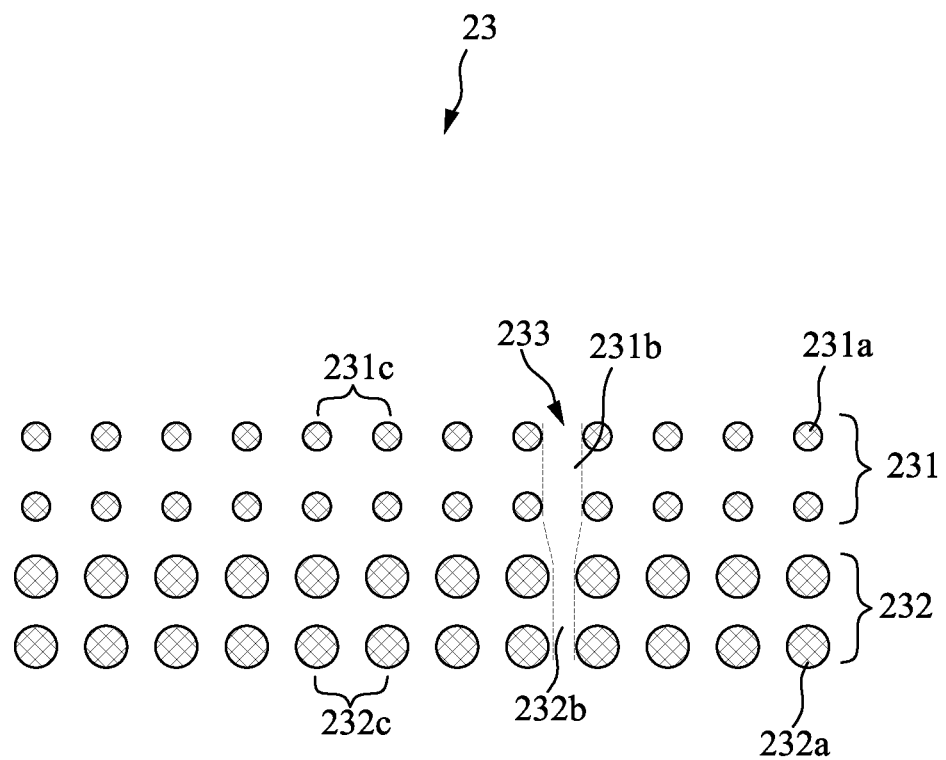
FIG. 4B is a schematic illustrating structure of the water-permeable layer according to another embodiment.

Please refer to FIG. 4B. In another type of embodiment, the diameter of the first thread 231a is smaller than the diameter of the second thread 232a, and the distance 231c on center line between the first threads in the first layer body 231 is equal to the distance 232c between on center line between the second threads in the second layer body 232.

Figure 4C:
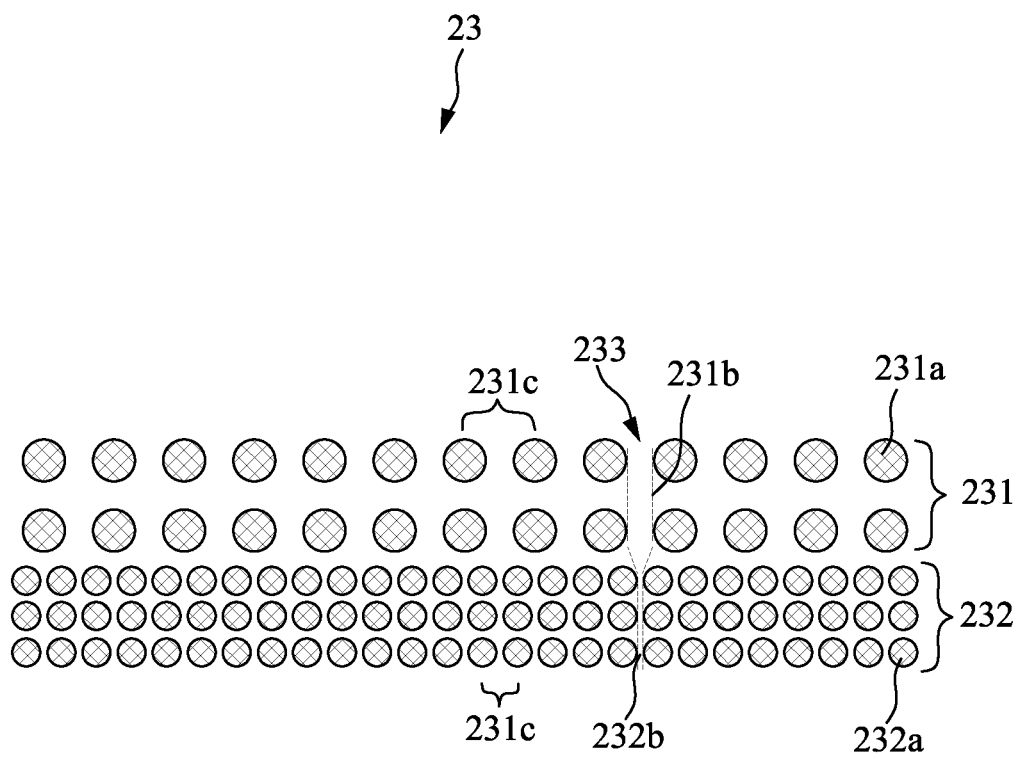
FIG. 4C is a schematic illustrating structure of the water-permeable layer according to yet another embodiment.

Please refer to FIG. 4C. In yet another type of embodiment, the diameter of the first thread 231a is larger than the diameter of the second thread 232a, and the distance 231c on center line between the first threads in the first layer body 231 is greater than the distance 232c on center line between the threads in the second layer body 232.

Wherein, the way to produce the aforementioned difference in thread diameter, in the previous embodiment, is to produce the difference in thread diameter by changing the number of monofilament strands used in twist into a unit thread. For example, when manufacturing the first thread 231a three strands of filament fibers are used in twist into the first thread 231a, and when manufacturing the second thread 232a seven strands of filament fibers are used in twist into the second thread 232a. In other embodiments, monofilament fibers with different diameters can be directly used.

As can be seen from the above description, the physiological pants 5 of the present invention is provided with a sanitary pad 2 that can be reused after air-dried, and in order to prevent the liquid stored in the water storage layer 22 in the sanitary pad 2 from easily leaving the sanitary pad 2 when being squeezed, the water-permeable layer 23 on the surface of the water storage layer 22 is provided with tapered holes 233 that allow liquid to easily pass through the water-permeable layer in single direction; wherein, as for the way to form the tapered hole 233 in the water-permeable layer 23, the water-permeable layer 23 has two layer bodies 231, 232 with water-permeable holes (231b, 232b) formed therein, and the sizes of the water permeable holes (231b, 232b) in each layer body are different; through contact between two layer bodies (231, 232), the water permeable holes (231b, 232b) of different sizes in the layer bodies are in contact with each other to jointly form the tapered holes 233 of the water-permeable layer 23. Wherein, in the manner of forming the water storage space 213, in a part of area, the waterproof layer 21 inside the sanitary pad 2 is bent, which makes the waterproof layer 21 through the bent portion on its both sides be a surrounding wall 211 to directly enclose the water storage space 213; in another part, the seal 206a attached to the edge of the sanitary pad 2 in conjunction with the waterproof layer 21 in the sanitary pad 2 are the surrounding wall 211 to create a water storage space 213.

The above-instanced embodiments are used for conveniently describing the present invention, not further to limit it. For the person skilled in the art of the disclosure, without departing from the concept of the disclosure, simple modifications or changes can be made and should be included in the following claims.

What is claimed is:

1. A physiological pants, comprising:
a clothing layer, constructing a piece of clothing, wherein the clothing is formed with a main opening for the torso to pass through and two secondary openings for the limbs to pass through;
a waterproof layer attached to the clothing layer, wherein the waterproof layer is formed as a surrounding wall to enclose a water storage space with a water absorbing opening;
a water storage layer arranged at the bottom of the water storage space;
a water-permeable layer arranged in the water storage space and contacts with a surface of the water storage layer close to the water absorbing opening, wherein the water-permeable layer containing an antibacterial agent; and
wherein the water-permeable layer includes a first layer body woven by a plurality of first threads and a second layer body woven by a plurality of second threads, the first layer body is formed with a plurality of first water-permeable holes, and the second layer body is formed with a plurality of second water-permeable holes smaller than the first water-permeable holes, so that a plurality of tapered holes are jointly formed inside the water-permeable layer by the first water-permeable holes and the second water-permeable holes, and
wherein a portion of the surrounding wall around the water absorbing opening extends toward the water absorbing opening, to thereby form a turned-inward portion, the turned-inward portion being connected to the surface of the water-permeable layer.

2. The physiological pants according to claim 1, wherein the thread diameter of the first thread is smaller than the thread diameter of the second thread, and the distance on centerline between the first threads in the first layer body is equal to the distance on centerline between the second threads in the second layer body.

3. The physiological pants according to claim 1, wherein the thread diameter of the first thread is smaller than the thread diameter of the second thread, and the distance on centerline between the first threads in the first layer body is larger than the distance on centerline between the second threads in the second layer body.

4. The physiological pants according to claim 1, wherein the thread diameter of the first thread is larger than the thread diameter of the second thread, and the distance on centerline between the first threads in the first layer body is larger than the distance on centerline between the second threads in the second layer body.

5. The physiological pants according to claim 1, wherein the waterproof layer, the water storage layer, and the water permeable layer together form a sanitary pad; and
   wherein two opposite sides of the sanitary pad are respectively formed as a curved portion corresponding to the shape of the secondary openings, and the remaining sides of the sanitary pad are respectively formed as two edges of different length, a first edge with and a second edge larger than the first edge.

6. The physiological pants according to claim 5, wherein the clothing layer is formed with an inner folder for covering the curved portion adjacent to the secondary opening, and the clothing layer has a first attachment area for attaching the first edge of the sanitary pad and a second attachment area for attaching the second edge of the sanitary pad.

7. The physiological pants according to claim 6, wherein the sanitary pad is fixed to the clothing layer through a plurality of seals, the sanitary pad is covered by a part of the seal, and one of the first attachment area and the second attachment area is covered by the other part of the seal.

8. The physiological pants according to claim 1, wherein the waterproof layer, the water storage layer and the water-permeable layer are connected to each other by stitching.

9. The physiological pants according to claim 1, wherein the water storage layer is a water-absorbing pad that can be reused after air drying.

10. The physiological pants according to claim 1, wherein the periphery of the water storage layer is formed as a connecting portion for connecting the water-permeable layer directly, so that a gap is formed between the water storage layer and the water-permeable layer for holding the liquid.

\* \* \* \* \*